United States Patent
Shen et al.

(10) Patent No.: US 7,412,281 B2
(45) Date of Patent: Aug. 12, 2008

(54) WIRELESS TRANSMITTED ELECTROCARDIOGRAM MONITORING DEVICE

(75) Inventors: Chien-Lung Shen, Chiayi (TW); Chun-Hui Li, Banciao (TW); Kun-Chi Hsieh, Kaohsiung (TW); Yen-Chun Cheng, Kuanghua Aelly (TW)

(73) Assignee: Taiwan Textile Research Institute, Taipei County (TW)

( * ) Notice: Subject to any disclaimer, the term of this patent is extended or adjusted under 35 U.S.C. 154(b) by 311 days.

(21) Appl. No.: 11/055,065

(22) Filed: Feb. 11, 2005
(Under 37 CFR 1.47)

(65) Prior Publication Data
US 2006/0111640 A1    May 25, 2006

(30) Foreign Application Priority Data
Nov. 23, 2004   (TW) ............................... 93136049 A

(51) Int. Cl.
*A61B 5/0402* (2006.01)

(52) U.S. Cl. ...................................... 600/509

(58) Field of Classification Search ............... 600/372, 600/382, 386, 388–390, 509; 607/60; 128/903
See application file for complete search history.

(56) References Cited

U.S. PATENT DOCUMENTS

| | | | |
|---|---|---|---|
| 6,381,482 B1 * | 4/2002 | Jayaraman et al. | 600/388 |
| 6,611,705 B2 * | 8/2003 | Hopman et al. | 600/509 |
| 6,645,008 B2 * | 11/2003 | Massey et al. | 439/581 |
| 6,941,775 B2 * | 9/2005 | Sharma | 66/202 |
| 6,970,731 B1 * | 11/2005 | Jayaraman et al. | 600/388 |
| 2005/0034485 A1 * | 2/2005 | Klefstad-Sillonville et al. | 66/171 |

* cited by examiner

*Primary Examiner*—Mark Bockelman
(74) *Attorney, Agent, or Firm*—Rosenberg, Klein & Lee

(57) ABSTRACT

A wireless transmitted electrocardiogram monitoring device is disclosed. A conductive fabric of the device features on that it is used to be a sensing component with characters of comfort, air permeability, softness, and stretchability thus achieves long-term signal measurement. The processing and transmission method of electrocardiogram signals is characterized in the wireless transmission of the electrocardiogram signals being detected. The signal receiving component (part) is for collecting data, displaying, storage, output and calculation of values. Therefore, a wireless transmitted electrocardiogram monitoring device is applied for long-term monitoring of the physical status of users.

9 Claims, 2 Drawing Sheets

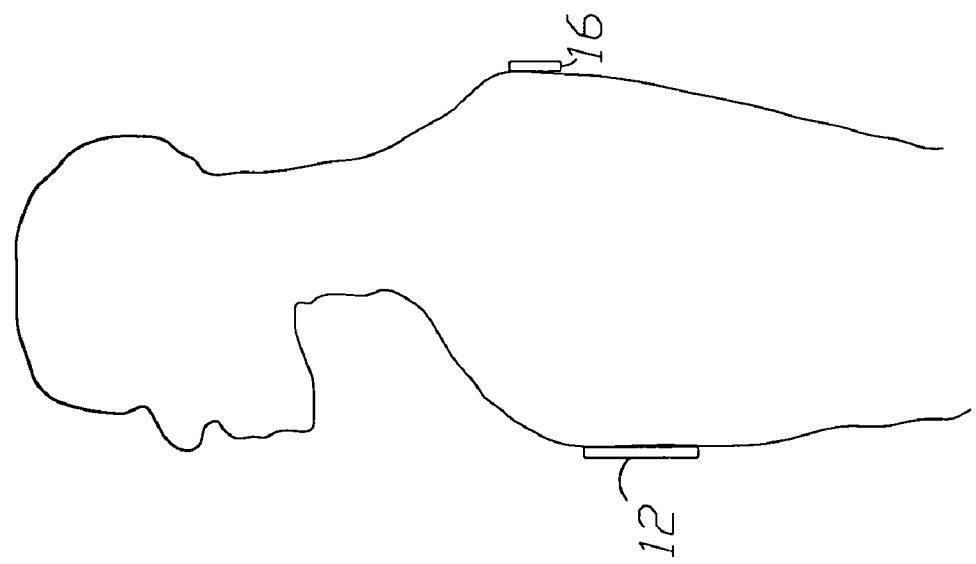
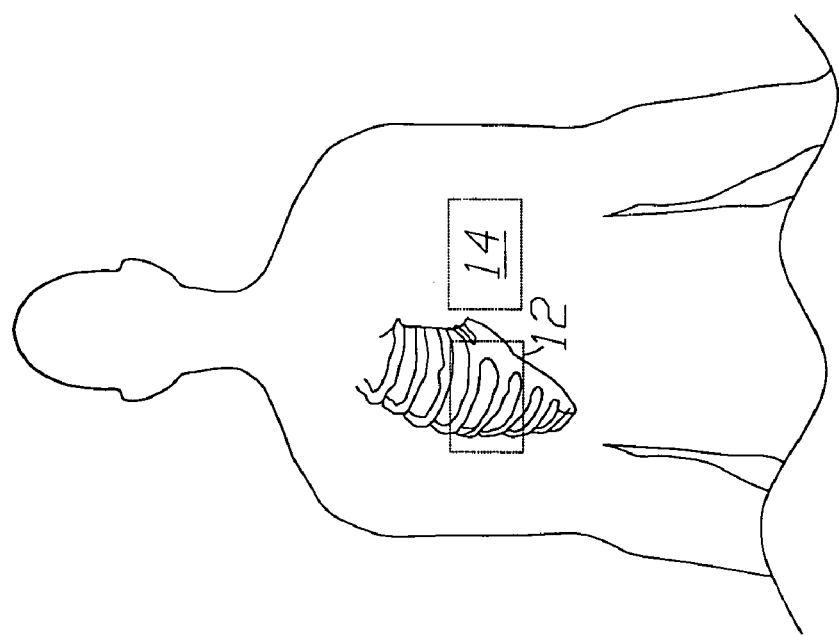

WIRELESS TRANSMITTED ELECTROCARDIOGRAM MONITORING DEVICE

BACKGROUND OF THE INVENTION

The present invention relates to a wireless transmitted electrocardiogram monitoring device which uses conductive fabric as electrodes in combination with wireless transmission for monitoring human electrocardiogram.

Refer to European Patent No. 0375440A1—"An electrode for use on living tissue", filed on 1990, an electrode for use in electrocardiography is disclosed. The device comprises a moisture vapour permeable porous material and an electrically conductive powder. The electrode may have an adhesive on one surface to facilitate attachment to a patient. As to another World Intellectual Property Organization patent No. 3094717A1—"TEXTILE ARTICLE HAVING ELECTRICALLY CONDUCTIVE PORTIONS AND METHOD FOR PRODUCING THE SAME", filed on 2003, a textile garment in the form of a bra or ladies top produced by circular knitting technique for detecting electrocardiogram is disclosed. The knitted construction includes electrically conductive yarn (fiber coated with metal) to form electrodes. The electrode is arranged in the inner layer, while the outer layer is an electrically insulated layer.

Moreover, in a Japanese patent publication No. 2000000221A2 named "SHEET FOR ELECTRODE", electrodes disposed inside a sheet for detecting electrocardiogram waveform and heart beat rate is disclosed. The electrodes are arranged near user's head and feet. The weft of the fabric is conductive yarn while the warp is non-conductive yarn. As to another Japanese Patent No. 60079957A2—"ENERGIZATION HEAD", applied on 1985, a fabric electrode made by fiber with diameter of 70 μm that is made of stainless filaments with diameter of 30 μm intertwisted with polyester (PET) fiber with diameter of 20 μm. The mixture of epoxy resin and aluminum hydroxide is heated to coat the fabric electrode. Refer to a further Japanese Patent No. 06070897A2—"ELECTRODES MOUNTING STRUCTURE IN VEST FOR ELECTROCARDIOGRAM MEASUREMENT", a vest for long-term detection of electrocardiogram is disclosed. The positions for measuring are around the front side of the chest and the belly. The vest is washable and with a slot for installation and disassembling of the external electrodes.

Moreover, refer to U.S. Pat. No. 4,608,987—"Apparatus for transmitting ECG data", A vest-like garment is provided. The device includes a front fabric panel with a plurality of apertures adapted for receiving associated electrodes, a horizontally stretchable rear panel, and a pair of vertically stretchable shoulder straps. Each of the electrodes is biased against the front panel for better electrical engagement with the skin of the user. Leads from each electrode may carry signals to a telephonic transmission unit, which is also equipped with emergency electrode handles. As to the U.S. Pat. No. 4,026,278 named "Electrode positioning and retaining belt", an electrode positioning belt for electrocardiogram is disclosed. An electrode positioning belt has Velcro loop fabric along the inner surface. Velcro hook fabric may be affixed to the back of the electrodes so they may be removable secured to the belt. The belt is wrapped around a body member. The ends of the belt overlap and a tab of hook fabric at one end of the belt on the outer surface is used to secure the belt. U.S. Pat. Nos. 4,729,377 and 4,580,572—"Garment apparatus for delivering or receiving electric impulses" disclosed a garment containing multiple conductive paths made of conductive cloth is used to connect an external electrical apparatus to various points on the skin of the wearer. The garment can be designed for electrical monitoring of physical status. A fabric, in the form of a woven or knitted fabric or garment disclosed in U.S. Pat. No. 6,381,482—"Fabric or garment with integrated flexible information infrastructure" is used for collecting, processing, transmitting and receiving information. The fabric allows a new way for information processing by selecting and plugging in (or removing) components from the fabric. The fabric can also be provided with sensors for monitoring physical aspects of the wearer. U.S. Pat. No. 6,145,551—"Full-fashioned weaving process for production of a woven garment with intelligence capability" discloses a woven garment made of only one single integrated fabric with armholes includes intelligence capability to monitor one or more body vital signs by including a selected sensing component or components.

Refer to Taiwanese patent publication No. 150548, a monitoring device for human heart beat, blood pressure, respiration and body temperature is disclosed. The monitoring device has a screen for displaying, voice and video signals for alarm and electrodes for detecting and amplifying weak signals from user's chest. As to Taiwanese patent publication No. 333445, a long-term monitoring method for cardiac activities is disclosed. The method includes pre-processing, reducing noise, and measuring threshold value of heart beating signals or noise in a dynamic way. Then the electrocardiogram waveforms are classified according to respective features of waves. Refer to Taiwanese patent publication No. 286538, it relates to a monitoring system for people in motion. The device, having a portable power supply and a microprocessor, measures and stores electrocardiogram and blood pressure data for diagnosis reference. A wireless measuring device for physical parameters is disclosed in Taiwanese patent publication No. 243179. The device includes a detector for body temperature and pulse, connected to a conversion circuitry for converting detected signals into physical parameters such as body temperature and pulse. Taiwanese patent publication No. 241002 named earphone-type detector for physical status discloses a detector composed by a detecting unit, in combination with a detecting module and a signal conversion module for receiving signals of physical status, and a beeper with warning voices for reminding users that the detected value is higher than normal range. Taiwanese patent publication No. 567831 discloses a Bluetooth® body temperature monitor consists of a Bluetooth® host and a Bluetooth® detect for body temperature detection. Taiwanese patent publication No. 526649 discloses a personal health monitor system using mobile phone for monitoring user's physical status. The users' data of physical status is collected and processed by monitoring program inside a portable information processor, then a corresponding message is produced to inform user about his/her health situation. Taiwanese patent publication No. 454502 discloses a monitor for detecting physical status with function of mobile phone. A mobile phone receiving physical signals displays values of signal on the phone screen in dot matrix way. Taiwanese patent publication No. 448761 discloses an underwear for monitoring heart beat arranged on chest. A contact point is attached on user's chest for detecting pulse from heart beats and then transmitted to the host in wireless way. Taiwanese patent publication No. 366796 discloses a wireless transmitter with infrared sensor for heat beat composed by a circuitry for reducing noise, heart heat sensor, and an amplifier transmitter. Taiwanese patent publication No. 275790 discloses a conductive piece attached on front side of the chest. By detecting electrical activity of heart form conductive piece placed on the surface of the skin, the detected signal is amplified and filtered through circuitry, then estimate heart rate by a heart beat detector. In Taiwanese patent No. M243180, strap structure for heat beat detector is disclosed. Two sheets of electrodes penetrate through air-permeable fabric and fixed on circuitry by metal rivets to form a strap tied on chest or other positions of body. Then the heart beat is estimated according to potential difference of pulse measured by the electrode contacted with the skin.

However, Taiwanese patents No. 150548, 333445, 286538, 243179, 241002, 567831, 526649, 454502, 448761, 366796, 275790, and M243180 has following shortcomings: 1. Most detectors of detecting devices or systems for physical status disclosed in above patents are portable or wearable for attaching on clothes or easy carrying. They are somewhat inconvenient for use. 2. The detectors of the above devices are made by hard material. Thus when they contact the skin of users, they can't adsorb moisture and eject sweat and they may cause problems of skin such as allergy. 3. The design of detectors on above sensing devices or systems has no softness and comfort so that they are not suitable for long-term or nonstop monitoring because they may cause skin discomfort. 4. The appearance of above monitoring devices or systems is easily be seen or attended and the devices are not minimized. Thus there must be some space for accommodating the devices or held by users. Thus the wearing of the devices causes some interference for users and can't be used without being feeling of devices.

Furthermore, the disadvantages of U.S. Pat. No. 4,608,987, U.S. Pat. No. 4,580,572, European patent No. 375440A1, Japanese patent No. 6070897A2, and Japanese patent No. 60079957A2 are: (1) The detecting component in the soft goods of above patents is made of cold and hard metal. When the detecting component touches user's skin, it may cause uncomfortable feelings. (2) The detector and the controller are connected by external wires (nonconductive fiber) so that the storage and breakage of these external wirings cause inconvenience of users. (3) The electrodes or detecting component composed by fibered porous material is not popular on the market. And the features (such as strength, elasticity, and absorption) of the material are far more less than the yarn. (4) The fabric electrodes on above soft goods are processed and hardened. When being applied to a polarized electrode, it is durable and thus is not suitable for long-term use. (5) The above soft goods with detection function need to be assembled with external electrodes through complicated steps for detection. Thus they can't be applied frequently on daily lives.

In addition, the shortcomings of the Japanese patent publication No. 2000000221A2, U.S. Pat. No. 6,381,482, U.S. Pat. No. 6,145,551 and WO patent No. 3094717A1 are:

(1) The soft goods mentioned in above patents are not portable or without the convenience of wear. (2) The detectors inside above soft goods need to combine with large area of fabric for achieving substantial effect.

Thus there is a need to provide a device having electrodes with features of comfort, air permeability, softness, and stretchability and signals being detected are transmitted in wireless way so as to avoid feelings of being tied and suitable for long-term monitoring of users' physical status.

SUMMARY OF THE INVENTION

Therefore it is a primary object of the present invention to provide a wireless transmitted electrocardiogram monitoring device which includes electrodes made of conductive fabric with features of comfort, air permeability, softness, and stretchability as well as wireless transmission for long-term monitoring of users' physical signals.

It is another object of the present invention to provide a wireless transmitted electrocardiogram monitoring device which uses at least three electrodes made of conductive fabric, wherein two electrodes are disposed on the fourth rib (counting inferiorly from the anterior of the rib cage—as is well known to one having ordinary skill in the art) of right and left chest respectively and one electrode is arranged on the back of a patient. The three electrodes made of conductive fabric are connected with textile by weaving so as to avoid feelings of being bound.

It is a further object of the present invention to provide a wireless transmitted electrocardiogram monitoring device that transmits monitoring data to a portable device such as PDA (personal digital assistant) in wireless way. Because the size of the portable device can be minimized with quite small volume so that it's convenient to be arranged—for example by handhold or in the pocket and is suitable for long-term monitoring.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein

FIG. 2A is a schematic diagram showing the front position of electrodes made of conductive fabric being disposed in accordance with the present invention;

FIG. 2B is a schematic diagram showing the rear position of electrodes made of conductive fabric being disposed in accordance with the present invention;

DETAILED DESCRIPTION OF THE PREFERRED EMBODIMENT

Figure 1:
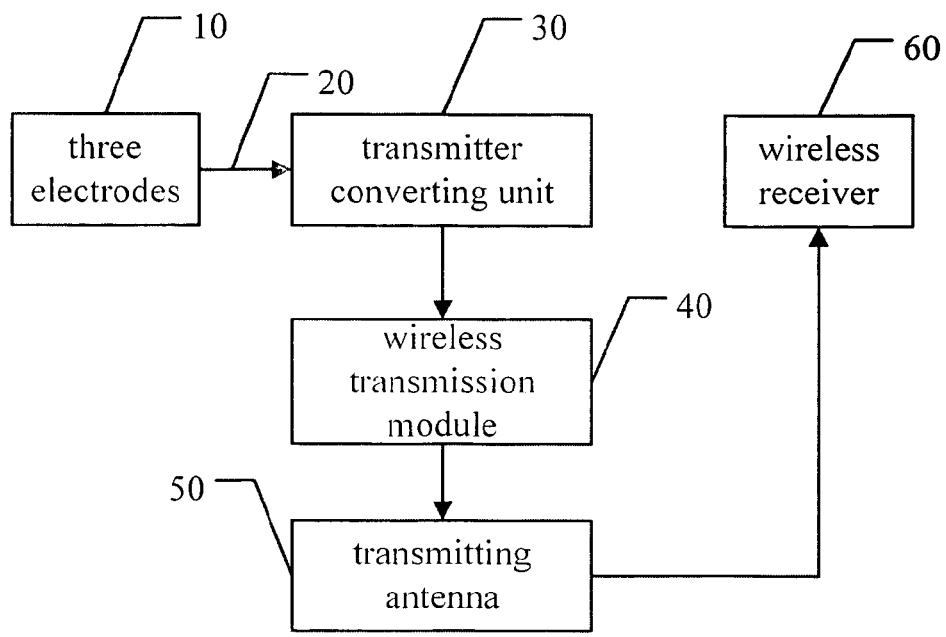
FIG. 1 is a block diagram of a preferred embodiment in accordance with the present invention.

Refer to FIG. 1, FIG. 2A & FIG. 2B a preferred embodiment of the present invention is disclosed. A wireless transmitted electrocardiogram monitoring device in accordance with the present invention consists of a conductive fabric electrode unit 10 having at least three electrodes 12, 14, and 16 made of conductive fabric, the conductive fabric having conductive fiber and nonconductive fiber, a transmitter converting unit 30 connected to the three electrodes of the conductive fabric electrode unit 10 by at least three strands of conductive yarn 20 respectively; the transmitter converting unit 30 receives an input signal and converts it into a transmitted signal; a wireless transmission module 40 for receiving the transmitted signal and producing a corresponding wireless signal; and a transmitting antenna 50 receiving the wireless signal and transmitting it into a wireless receiver 60.

The features of the electrodes made of conductive fabric are described as followings:

Processed by plain weave or knitting with surface resistance preferably less than 20 $\Omega/cm^2$ and more preferably approximately: 0.16 $\Omega/cm^2$;

specification of fiber:

| |
|---|
| conductive fiber (A): yarn coated with silver 150D/72f |
| nonconductive fiber (B): PET 150D/48f |
| processing conditions: 2(A)1(B) 214 TPM |

Refer to FIG. 2A & FIG. 2B, a schematic drawing shows positions of the electrodes made of conductive fabric in accordance with the present invention. Two electrodes 12, 14 are disposed near the fourth rib (counting inferiorly) of the right and left chest respectively, while one electrode 16 is arranged on the rear side of an underwear, close to the skin.

Figure 3:
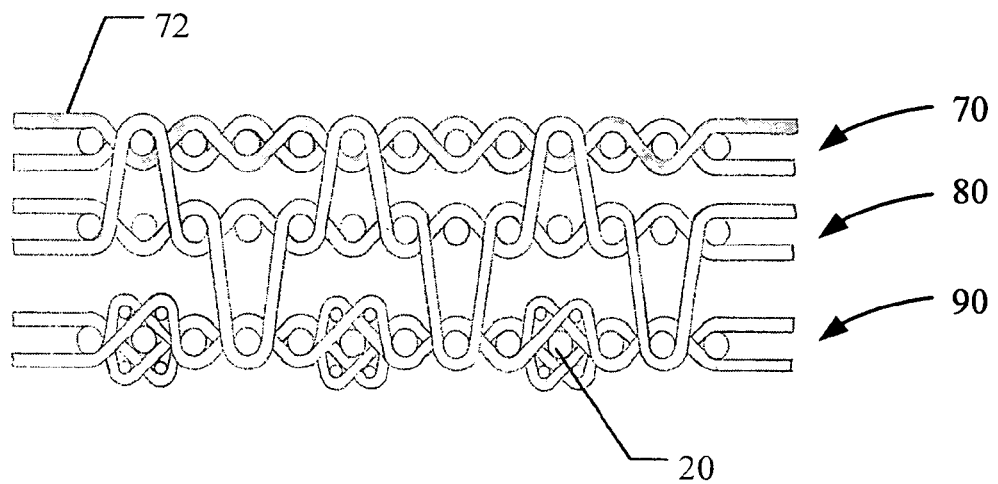
FIG. 3 is a schematic diagram showing the structure of fabric in accordance with the present invention to protect users from electromagnetic waves.

Refer to FIG. 3, a preferred embodiment of the present invention that protects users from electromagnetic waves is disclosed. As shown in the figure, outside the electrodes of the conductive fabric electrode unit 10 and the conductive yarn 20, there are: an electromagnetic waves shielding layer 70, an isolation layer 80, and a conductive wire fixing layer 90 from outside in. The electromagnetic interference shield layer 70 is a shield for preventing electromagnetic waves, woven by conductive yarn 72, while the isolation layer 80 is woven by nonconductive yarn. The conductive wire fixing layer 90 is made by laminated fabric that is double layers structure for fixing and securing the conductive yarn 20 or the conductive yarn of the conductive fabric electrode unit 10. The composition and weaving conditions are as following:

| | |
|---|---|
| 1. Wales Per Inch: | 180 (the number of wales)/inch |
| 2. Course Per Inch: | 180 (the number of courses)/inch |
| 3. warp: | A = pet 150 d    B = the silver fiber |
| 4. weft: | A = pet 150 d    B = the silver fiber |
| 5. arrangement of warp: | A108, (1B2A)*88, A108, (1B2A)*70, A108, (1B2A)*88, A108 |
| 6. harness draft: | (1.2.3.4.5.6.1.7.3.4.8.6)*24, [(1.9.3.4.10.6.1.11.3.4.12.6.)*11, (1.9.3.4.10.6.1.13.1.415.16.3.4.13.14.15.16.6.17), (1.13.1.415.16.3.4.13.14.15.16.6.1.11.3.4.12.6), (1.9.3.4.10.6.1.11.3.4.12.6.)*11, (1.2.3.4.5.6.1.7.3.4.8.6)*2]*3, (1.2.3.4.5.6.1.7.3.4.8.6)*22 |
| 7. arrangement of weft: | 1B2A |

When a mobile phone in communication is close to a patient, it interferes with electrocardiogram signals, especially gain in the frequency of 100 Hz and 120 Hz, the electrocardiogram in spectrum is seriously affected. During the measurement process, except the user, if other people contact or approach the transmission pathway of the electrocardiogram signals, the interference of 60 Hz from environment will be introduced into the signals. However, no matter the interference either from contacts or electromagnetic waves, the quality of signals is dramatically improved after using products of the present invention.

Quantization Results

| | AC interference | Electromagnetic interference | |
|---|---|---|---|
| | gain at 60 Hz (unit) | gain at 100 Hz (unit) | gain at 120 Hz (unit) |
| Standard transmission line" | 0.4729 | 10.3239 | 1.966 |
| Product of embodiment according to the present invention | 0.1233 | 0.0639 | 0.0273 |

Embodiment 1

Electrocardiogram Monitoring Strap

C. electrocardiogram detective unit
1. Three electrodes made of conductive fabric are sewed on a chest belt respectively;
2. Three conductive buttons are strung on three pieces of conductive fabric respectively for providing conductive pathway of electrodes made of conductive fabric and the electrocardiogram monitoring device with Bluetooth® interface;
3. The end product is worn on the chest and signals being detected are transmitted to a PDA through the Bluetooth® interface.

D. The PDA is fixed on a watchband so that it can be carried on limbs of users.

Embodiment 2

Electrocardiogram Monitoring Costume

B. electrocardiogram detective unit
5. In the three electrodes made of conductive fabric, two pieces of conductive fabric are sewed at the position near the fourth rib of right and left chest respectively while the third piece of conductive fabric is arranged on back of an underwear, close to the skin.
6. Three conductive buttons are strung on three pieces of conductive fabric respectively through the integrated conductive yarn for providing conductive pathway of electrodes made of conductive fabric and the electrocardiogram monitoring device with Bluetooth® interface.
7. The conductive yarn has no contact with user's skin, only the fabric or yarn contacts the skin. The three conductive buttons also don't touch the skin, but through the fabric or isolation material.
8. The end product is worn on the upper body and the detected signals are transmitted to the PDA through the Bluetooth® interface.

B. A pocket on sports coat is used as a carrier of a PDA for being carried by users conveniently.

Embodiment 3

Electrocardiogram Monitoring Waist Belt

A. electrocardiogram detective unit
1. In the three electrodes made of conductive fabric, two pieces of conductive fabric are sewed at the position near the fourth rib of right and left chest respectively while the third piece of conductive fabric is arranged on back of an underwear, close to the skin.

2. Three conductive buttons are strung on three pieces of conductive fabric respectively through the integrated conductive yarn for providing conductive pathway of electrodes made of conductive fabric and the electrocardiogram monitoring device with Bluetooth® interface.
3. The conductive yarn has no contact with user's skin, only the fabric or yarn contacts the skin. The three conductive buttons also don't touch the skin, but through the fabric or isolation material.
4. The end product is worn on the upper body and signals being detected are transmitted to a PDA through the Bluetooth® interface.

B. A waist belt is used as a carrier of a PDA for being carried by users easily.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A wireless transmitted electrocardiogram monitoring device comprising:
   at least three electrodes made of conductive fabric having conductive fiber and nonconductive fiber;
   a transmitter converting unit connected to the three electrodes by at least three strands of conductive yarn respectively for receiving an input signal and converting it into a transmitted signal;
   a wireless transmission module for receiving the transmitted signal and producing a corresponding wireless signal; and
   a transmitting antenna for receiving the corresponding wireless signal and transmitting the corresponding wireless signal into a wireless receiver;
   wherein, outside the electrode made of conductive fabric and the conductive yarn, there are an electromagnetic interference shield layer, an isolation layer, and a conductive wire fixing layer from outside in.

2. The wireless transmitted electrocardiogram monitoring device as claimed in claim 1, wherein surface resistivity of the electrode made of conductive fabric is less than 20 $\Omega/cm^2$.

3. The wireless transmitted electrocardiogram monitoring device as claimed in claim 1, wherein the conductive yarn is adapted to no contact with a patient being monitored.

4. The wireless transmitted electrocardiogram monitoring device as claimed in claim 1, wherein at least two of the electrodes are adapted to be disposed on a fourth rib of right and left chest respectively while one electrode is adapted to be arranged on a back of a patient being monitored and is contacted therewith.

5. The wireless transmitted electrocardiogram monitoring device as claimed in claim 1, wherein the wireless receiver is connected to a remote terminal and wireless signals received by the wireless receiver are transmitted to the remote terminal for being executed.

6. The wireless transmitted electrocardiogram monitoring device as claimed in claim 1, wherein the wireless receiver is a personal digital assistant having a Bluetooth® module.

7. The wireless transmitted electrocardiogram monitoring device as claimed in claim 1, wherein the electromagnetic interference shield layer is a shield woven by conductive yarn for preventing electromagnetic waves.

8. The wireless transmitted electrocardiogram monitoring device as claimed in claim 1, wherein the isolation layer is woven by nonconductive yarn.

9. The wireless transmitted electrocardiogram monitoring device as claimed in claim 1, wherein the conductive wire fixing layer is made by laminated fabric that is a double layered structure for fixing and securing the conductive yarn.

* * * * *